United States Patent [19]

Lee

[11] Patent Number: 5,258,044
[45] Date of Patent: Nov. 2, 1993

[54] ELECTROPHORETIC DEPOSITION OF CALCIUM PHOSPHATE MATERIAL ON IMPLANTS

[75] Inventor: Dosuk D. Lee, Brookline, Mass.

[73] Assignee: Etex Corporation, Cambridge, Mass.

[21] Appl. No.: 828,011

[22] Filed: Jan. 30, 1992

[51] Int. Cl.$^5$ .................. A61F 2/54; A61F 2/28; A01N 1/02; A61K 1/02
[52] U.S. Cl. ..................... 623/66; 623/16; 427/2; 606/76
[58] Field of Search ............. 623/16, 60; 606/76; 427/2

[56] References Cited

U.S. PATENT DOCUMENTS

| | | |
|---|---|---|
| Re. 33,161 | 2/1990 | Brown et al. . |
| Re. 33,221 | 5/1990 | Brown et al. . |
| 3,443,261 | 5/1969 | Battista et al. ............ 623/16 |
| 3,892,648 | 7/1975 | Phillips et al. ............ 606/76 X |
| 3,892,649 | 1/1975 | Phillips et al. . |
| 4,222,128 | 9/1980 | Tomonaga et al. . |
| 4,503,157 | 3/1985 | Hatahira et al. . |
| 4,596,574 | 6/1986 | Urist et al. . |
| 4,612,053 | 9/1986 | Brown et al. . |
| 4,626,392 | 12/1986 | Kondo et al. ............ 623/16 X |
| 4,693,986 | 9/1987 | Vit et al. ............ 623/16 X |
| 4,708,652 | 11/1987 | Fujiu et al. . |
| 4,722,870 | 2/1988 | White . |
| 4,868,287 | 9/1989 | Sikes ............ 530/324 |
| 4,880,610 | 11/1989 | Constantz . |
| 4,944,754 | 7/1990 | Linkow et al. ............ 623/16 |
| 4,950,294 | 8/1990 | Hakamatsuka . |
| 4,969,913 | 11/1990 | Ojima . |
| 4,988,362 | 1/1991 | Toriyama et al. . |
| 4,990,163 | 2/1991 | Ducheyne et al. ............ 623/16 X |
| 5,030,474 | 7/1991 | Saita et al. ............ 623/16 X |
| 5,125,971 | 6/1992 | Nonami et al. ............ 433/228.1 |

Primary Examiner—David Isabella
Assistant Examiner—Dinh X Nguyen
Attorney, Agent, or Firm—Fish & Richardson

[57] ABSTRACT

The invention features a method for preparing coated implants. The method includes the steps of: (a) providing a gel of amorphous calcium phosphate having a calcium to phosphorous ratio of 0.5 to 1.6; (b) dispersing the gel of amorphous calcium phosphate in an aqueous liquid to form a colloidal mixture which is between 60% and 99% by weight water; (c) immersing an implant to be coated in the colloidal mixture; and (d) with the implant acting as an anode, electrodepositing material in the colloidal mixture on the implant to form a substantially uniform coating.

8 Claims, No Drawings

ELECTROPHORETIC DEPOSITION OF CALCIUM PHOSPHATE MATERIAL ON IMPLANTS

BACKGROUND OF THE INVENTION

The field of the invention is coatings for orthopedic implant materials.

Orthopedic implants are commonly coated with bioactive ceramics, particularly calcium phosphate (a naturally-occurring bone mineral), to provide a surface suitable for the ingrowth of bone tissue. The ingrowth of bone tissue results in secure fixation of the implant to existing bone. It is known in the art that coatings may be applied to an implant by slip casting, plasma spraying, and electrophoretic deposition.

Ducheyne et al. (U.S. Pat. No. 4,990,163) disclose the use of powdered calcium phosphate compounds dissolved in isopropanol for electrophoretic deposition of a bioactive coating on implant surfaces. The coating is said to have a high dissolution rate.

Phillips et al. (U.S. Pat. No. 3,892,648) disclose the electrophoretic deposition of bone particles in a collagen-bearing medium on orthopedic implants. Collagen fibrils are dispersed in a gelatin medium; the resulting gelled collagen is next dispersed in a water/glycerine solution, and finely divided bone is added to the solution. The solution is used in an electrophoretic deposition process to create a coating of bone and collagen on an implant surface.

SUMMARY OF THE INVENTION

In general, the method features a method for preparing coated implants. The method includes the steps of: (a) providing a gel of amorphous calcium phosphate having a calcium to phosphorous ratio of 0.5 to 1.6; (b) dispersing the gel of amorphous calcium phosphate in an aqueous liquid to form a colloidal mixture which is between 60% and 99% by weight water; (c) immersing an implant to be coated in the colloidal mixture; and (d) with the implant acting as an anode, electrodepositing material in the colloidal mixture on the implant to form a substantially uniform coating. The method is especially well-suited to coating of metals for use as orthopedic implants. The gel has a calcium to phosphorous ratio of between 0.5 and 1.6 at a pH of between 8 and 14, preferably 11.

In preferred embodiments, the gel is comprised of a mixture of calcium nitrate, di-ammonium hydrogen phosphate, and ammonium hydroxide; and the aqueous liquid is essentially water.

In another preferred embodiment, the method includes the step of sintering the coated implant subsequent to step (d).

In a more preferred embodiment, the sintering is performed at between 600° C. and 1350° C. In a still more preferred embodiment, the sintering is performed in air.

The method of the invention creates a uniform finely-crystalline on the implant surface. The coated implant can be sintered. The resulting coating is fine-grained, well-crystallized hydroxyapatite. The surface has superior mechanical strength and is substantially insoluble in aqueous environments.

Other features and advantages of the invention will be apparent from the following description of the preferred embodiments thereof, and from the claims.

DETAILED DESCRIPTION

Described below are techniques for preparing a gel of amorphous calcium phosphate, preparing a colloidal mixture of the gel and an aqueous solution, electrophoretically depositing material in the solution on an implant surface, and sintering the coated material to produce a coating of hydroxyapatite.

A gel of amorphous calcium phosphate is prepared from an aqueous solution of calcium nitrate [$Ca(NO_3)_2$], di-ammonium hydrogen phosphate [$(NH_4)_2HPO_4$], and ammonium hydroxide [$(NH_4)(OH)$] as described by LeGeros (Calcium Phosphate in Oral Biology and Medicine, *Monographs in Oral Science*, vol. 15, Meyers, ed., Basel: Karger, 1991, p. 201). Briefly, a 0.2 M to 0.5 M (preferably 0.32 M) solution of calcium nitrate is made basic by the addition of 5% to 10% (preferably 7.3%) ammonium hydroxide by volume; a 0.1 M to 0.3 M (preferably 0.15 M) solution of di-ammonium hydrogen phosphate is made basic by the addition of 1% to 5% (preferably 3.1%) ammonium hydroxide by volume. One part of the calcium nitrate solution is quickly added to 2 to 3 parts (preferably 2.4 parts) of the di-ammonium hydrogen phosphate solution with vigorous stirring to create a solution having a calcium to phosphorous ratio of 0.5 to 1.6, preferably approximately 0.9. The pH of the resulting solution is between 8 and 14 (preferably 11). The solution rapidly develops into a colloidal gel which is filtered and washed in water to remove excess ammonium ions. Infrared spectroscopy may be used to check for the presence of excess ammonium ions. Washing for approximately 24 hours is adequate. An electrophoretic solution is prepared by mixing 1 to 40% by weight gel with water. The solution is stirred vigorously to disperse the gel into a fine colloidal solution. The solution is used in the electrodeposition described below.

The material to be coated is thoroughly cleaned prior to electrodeposition. In the case of titanium alloys, this can be accomplished by polishing with emery cloth, followed by ultrasonic cleaning in alcohol and etching in a dilute solution of nitric and hydrofluoric acid. During electrodeposition the material to be coated serves as the anode and is suspended in the above-described colloidal solution. The deposition itself is conducted under conditions of constant current at 1 to 100 mA, preferably approximately 5 mA. Alternatively, the deposition may be conducted under conditions of constant voltage at 1 to 35 volts, preferably approximately 32 volts. During deposition the temperature of the solution may be between room temperature and 100° C., preferably approximately 40° C.

The distance between the anode and cathode during deposition is preferably between 1 and 20 cm. A preferred geometry places the anode to be coated at the center of a radially symmetric array of cathodes or a cylindrical cathode.

The above-described procedure produces a uniform, finely crystalline coating of calcium phosphate on the substrate which is next sintered at 600° C. to 1350° C. in air (preferably 900° C.) for 1 to 12 hrs, preferably approximately 2.5 hrs.

Analysis of the coating by x-ray diffraction and infrared spectroscopy indicates that the coating created is composed of fine-grained, well-crystallized hydroxyapatite. Tests of shear and tensile strength indicates that the coating produced in this fashion has excellent mechanical properties.

What is claimed is:

1. A method for preparing a coated implant, said method comprising the steps of:
   (a) providing a gel of amorphous calcium phosphate having a molar ratio of calcium to phosphorous of 0.5 to 1.6;
   (b) dispersing said gel of amorphous calcium phosphate in an aqueous liquid to form a colloidal mixture of said amorphous calcium phosphate and said aqueous liquid which comprises between 60% and 99% by weight water;
   (c) immersing an implant to be coated in said colloidal mixture; and
   (d) with said implant used as an anode, electrodepositing said amorphous calcium phosphate on said implant to form a substantially uniform coating.

2. The method of claim 1 wherein said gel is comprised of a mixture of calcium nitrate, di-ammonium hydrogen phosphate, and ammonium hydroxide having a calcium to phosphorous ratio of between 0.5 and 1.6.

3. The method of claim 1, further comprising sintering said coated implant subsequent to step (d).

4. The method of claim 3 wherein said sintering step is performed at between 600° and 1350° C.

5. The method of claim 4 wherein said sintering step is performed in air.

6. The method of claim 1 wherein said aqueous liquid is essentially water.

7. An implant produced by the process as in one of claims 1-6.

8. An implant comprising an electrodeposited layer of an amorphous calcium phosphate coating, wherein said amorphous calcium phosphate coating has a molar ratio of calcium to phosphorous of 0.5 to 1.6.

* * * * *